US006468313B1

(12) United States Patent
Claeson et al.

(10) Patent No.: US 6,468,313 B1
(45) Date of Patent: Oct. 22, 2002

(54) IMPLANTS AND METHOD OF MAKING

(75) Inventors: Anne Claeson, Minneapolis; Thomas Odland, Lino Lakes, both of MN (US)

(73) Assignee: Bio-Vascular, Inc., St. Paul, MN (US)

( * ) Notice: Subject to any disclaimer, the term of this patent is extended or adjusted under 35 U.S.C. 154(b) by 0 days.

(21) Appl. No.: 09/672,799

(22) Filed: Sep. 22, 2000

Related U.S. Application Data

(63) Continuation of application No. PCT/US99/06062, filed on Mar. 19, 1999.
(60) Provisional application No. 60/078,985, filed on Mar. 23, 1998.

(51) Int. Cl.$^7$ .................................................. A61F 2/02
(52) U.S. Cl. ................................ 623/23.72; 623/13.17; 623/14.12
(58) Field of Search ............................ 623/14.12, 6.64, 623/905, 23.72, 11.11, 13.17, 23.76, 23.58; 433/173, 174, 201.1

(56) References Cited

U.S. PATENT DOCUMENTS

| | | | |
|---|---|---|---|
| 4,456,589 A | * | 6/1984 | Holman et al. ............... 424/95 |
| 4,755,593 A | * | 7/1988 | Lauren |
| 4,915,113 A | | 4/1990 | Holman |
| RE34,307 E | | 7/1993 | Perry |
| 5,503,638 A | | 4/1996 | Cooper et al. |
| 5,549,628 A | | 8/1996 | Cooper et al. |
| 5,575,803 A | | 11/1996 | Cooper et al. |
| 5,584,880 A | * | 12/1996 | Martinez ..................... 623/4.1 |
| 5,782,914 A | * | 7/1998 | Schankereli .............. 623/11.11 |
| 6,063,117 A | * | 5/2000 | Perry .......................... 623/4.1 |
| 6,176,880 B1 | * | 1/2001 | Pluohar et al. |
| 6,187,041 B1 | * | 2/2001 | Garonzik .................... 623/4.1 |

FOREIGN PATENT DOCUMENTS

| | | |
|---|---|---|
| EP | 0 364 871 | 10/1989 |
| WO | PCT/AU84/00206 | 4/1985 |
| WO | PCT/US98/25674 | 6/2000 |

OTHER PUBLICATIONS

M. Valente, et al., "Detoxified Glutaraldehyde Crosslinked Pericardium: Tissue Preservation and Mineralization Mitigation in a Subcutaneous Rat Model", (*J. Heart Valve Dis.* 1998 May;7(3);283–91).

C. Stacchino et al., "Detoxification Process for Glutaraldehyde–treated Bovine Pericardium; Biological, Chemical and Mechanical Characterization", *J Heart Valve Dis.* 1998 Mar. 7(2):190–4.

* cited by examiner

*Primary Examiner*—Pedro Philogene
(74) *Attorney, Agent, or Firm*—Frederickson & Byron, P.A.

(57) ABSTRACT

An implant material in the form of a natural animal tissue crosslinked into a pre-formed shape, the tissue being adapted to substantially retain its shape when implanted into a body. Suitable tissues include fibro-serous membranes such as pericardium. Suitable crosslinking agents include aldehydes (e.g., glutaraldehyde), epoxides, isocyanates, carbodiimides, isothiocyanates, glycidalethers, and acyl azides. The implant material can be processed in either the supple or non-supple form, by the judicious use of ethanol and/or other dehydrating solutions in the course of its processing.

27 Claims, 7 Drawing Sheets

PAGE 1

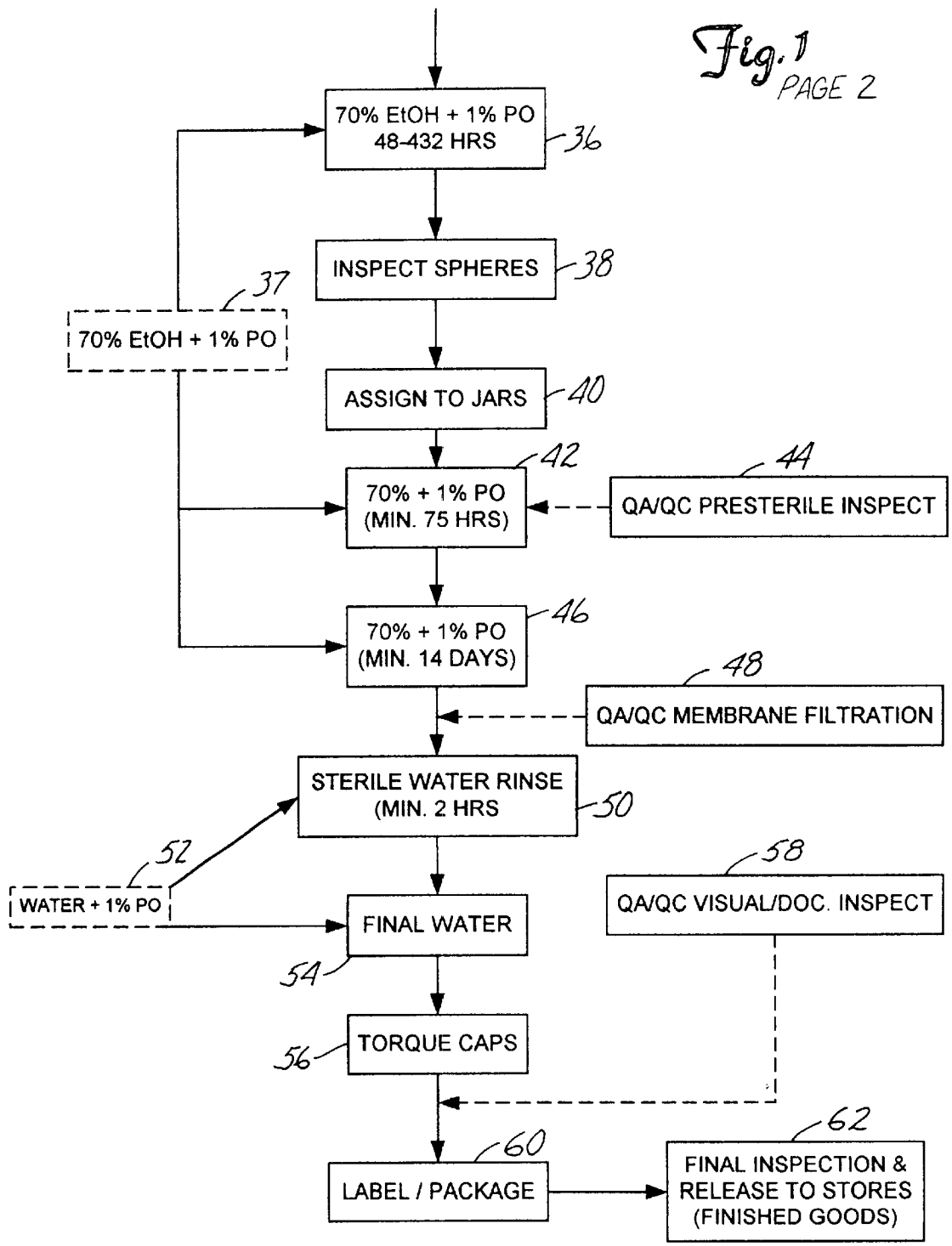

PAGE 1
REGULAR PREFORMED FLOWCHART

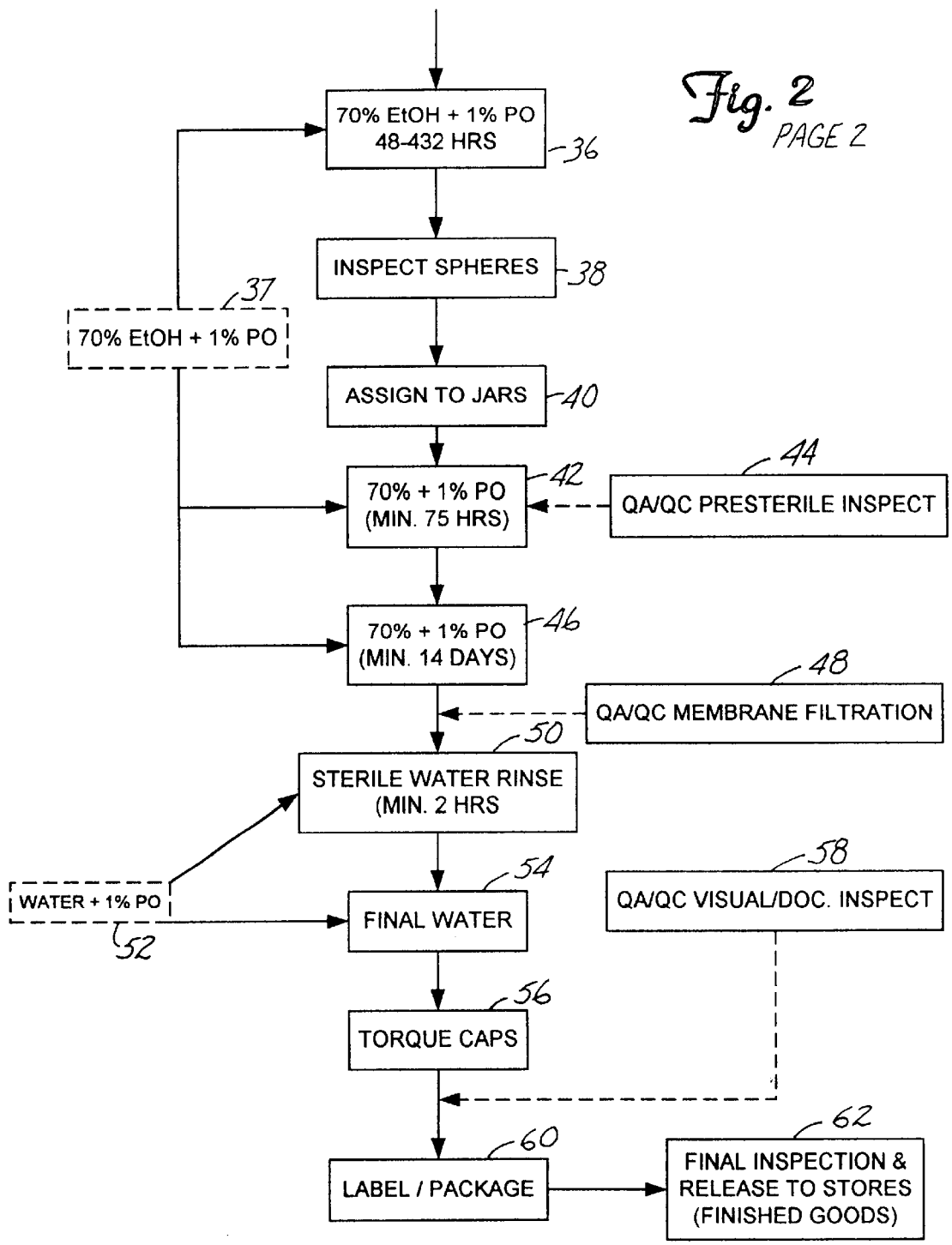

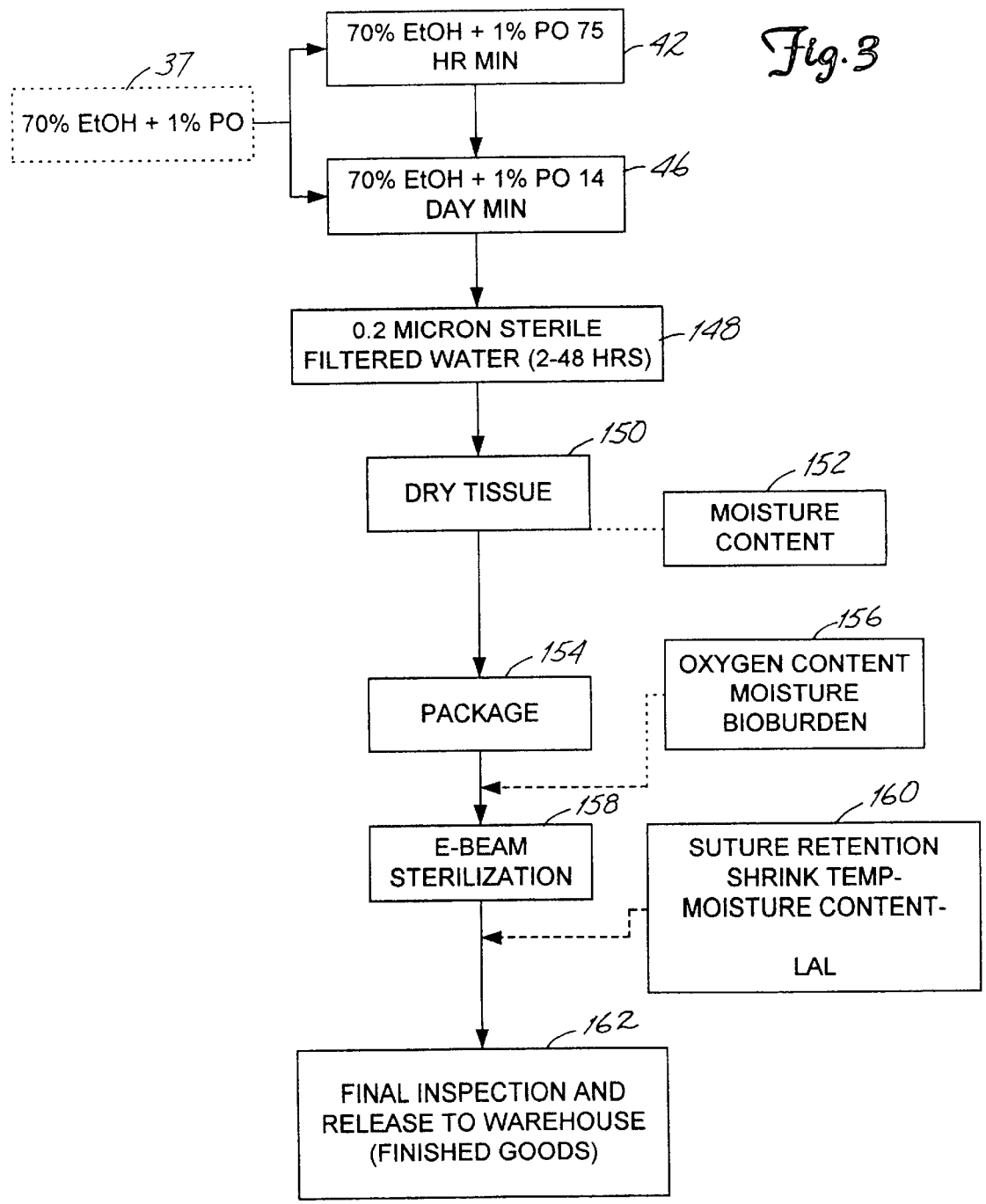

Fig. 6a
Wrapped Implant
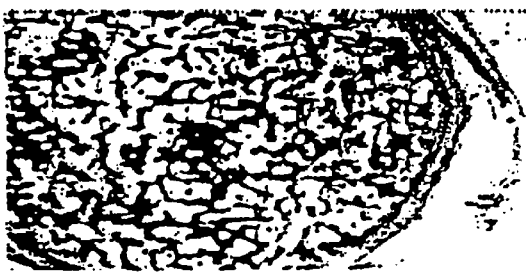
Peri-Guard Wrapped Implant (2.5X)
Complete fibrovascular ingrowth

Fig. 6b
Disrupted lamellae of Peri-Guard with adjacent inflammatory reaction (25X)

Fig. 7a
Sclera Wrapped Implant
Sclera wrapped implant (2.5X)
Complete fibrovascular ingrowth

Fig. 7b
Minimal Disruption of lamellae of sclera with minimal adjacent inflammatory reaction (25X)

Fig. 8a
Non-Wrapped Implant
Non-wrapped implant (3.3X)
Zone of implant avascularity with inflammatory coagulum

Fig. 8b
Normal fibrovascular tissue and adjacent inflammatory coagulum (25X)

IMPLANTS AND METHOD OF MAKING

CROSS-REFERENCE TO RELATED APPLICATIONS

The present application is a continuation of and claims priority to International Application No. PCT/US99/06062 (published as International Publication No. WO 99/48540), filed Mar. 19, 1999 and designating the United States, which in turn claims priority from provisional application having U.S. Ser. No. 60/078,985, filed Mar. 23, 1998, the entire disclosure of which is incorporated herein by reference.

BACKGROUND OF THE INVENTION

1. Field of the Invention

In one aspect, the present invention relates to the use of natural tissues as implantable materials for medical-surgical use. In a related aspect the present invention is directed generally to wraps for implants including intra orbital prosthetic ocular implants designed to be accommodated in the orbital cavity after enucleation and, particularly, an improved pre-formed wrap and method of making the wrap for an orbital implant that simplifies the implant procedure and produces a compatible and comfortable wrapped implant prosthesis. The invention contemplates the use of preformed, processed pouches for the wraps that are substantially spherical and which are constructed of natural bio-compatible animal tissue, preferably bovine pericardial tissue.

2. Related Art

Eyes severely damaged due to disease or trauma may have to be partially or totally removed and replaced by implant prostheses. In this manner, the damaged eye may be eviscerated, a procedure in which all of the inner contents are removed or, an enucleation may have to be performed in which the entire eyeball is removed after severing it from the eye muscles and the optic nerve. Typically, an artificial implant is fitted into the orbital socket to replace the volume in the orbit that was lost when the eye was removed. To this an artificial eye is fitted which is also attached to the eye muscles so that it will track with the normal eye. With evisceration, a sufficient amount of the patient's own tissue may be available to contain or isolate the implant. In the case of enucleation, however, nothing remains inwardly of the patient's own tissue to encase the implant prosthesis and a separate wrap must be provided.

The typical ocular orbital implants are made from natural or non-natural materials of various types including hydroxyapatite obtained from coral or manufactured by synthetic means, as illustrated in U.S. Pat. No. Re 34,307 to Perry. The implants also are also made from various synthetic polymer materials, such as a porous polyethylene. The generally spherical implants, in the case of an eviscerated eye, are normally inserted into the scleral sac of the patient's own eye which remains attached and the sac is sewn closed about the implant. If, however, an enucleation or total removal of the eye has been performed, a replacement for the scleral sac must also be used in order for the implant to be isolated in order to prevent a foreign body reaction and protected from infection. Many materials have been used for such replacement scleral sacs including material earlier removed from the patient or received from an eye bank. While these and other materials including flat sections of animal tissue have been used with some success, it is difficult and time-consuming to form such materials into the proper spherical shapes during surgical implantation procedures.

There remains a need for an orbital implant wrap or sac device which is pre-formed to the proper spherical shape with respect to receiving an ocular implant for replacement of a removed eyeball.

Accordingly, it is a primary object of the present invention to provide a pre-formed orbital implant wrap or sac for an ocular implant prosthesis that is pre-formed to fit an ocular prosthesis and the eye socket.

Another object of the present invention is to provide a pre-formed crosslinked wrap for an ocular prosthesis that is processed from bovine pericardial tissue.

Other objects and advantages will occur to those skilled in the art upon becoming familiar with the specification, drawings and appended claims herein.

On a separate subject, Applicant's own prior patents and applications related generally to the use of animal tissues (e.g., U.S. Pat. No. 4,456,589), including for such purposes as staple buttresses (U.S. Pat. Nos. 5,503,638; 5,549,628; 5,575,803; and vascular grafts (U.S. Pat. No. 4,915,113), and stent covers (International Application Serial No. PCT/US98/25674) the disclosures of each of which are incorporated herein by reference.,

SUMMARY OF THE INVENTION

In accordance with the present invention, it has been discovered that certain natural animal tissues, properly preserved and processed, present superior properties for pre-formed implants, including wraps. In the case of ocular orbital implants, in particular, it has been found that if the implant wraps are pre-formed in a spherical shape and the tissue processed or crosslinked, in the pre-formed shape a superior wrap is produced which facilitates the implant procedure. In particular, bovine pericardial tissue has been used quite successfully. The processed orbital implant wraps of the invention are sterile and ready to receive implants and can be readily situated and attached in place. They can be produced in all convenient sizes required.

The invention further contemplates a process for forming and crosslinking pre-shaped orbital implant wraps or spherical sacs which results in implantable sacs shaped to precisely receive spherical implants in a variety of sizes and to be received and secured to or as a replacement for the scleral sac of a patient.

It will be appreciated that the process for manufacturing orbital implant wraps in the pre-formed state in accordance with the process of the present invention results in an easier and less time consuming artificial eye implant procedure.

In the process of the present invention the orbital implant wraps are formed from pre-soaked or dehydrated animal tissue using generally spherical shaping forms of desired sizes. The generally spherical forms are wrapped with the material which is secured in place in a manner which preserves an implant inlet opening. The tissue is thereafter crosslinked in place, removed from the form and the opening shaped in the pre-formed, generally spherical sac. The wraps are then rinsed, sterilized and packaged for shipment in a water solution or, alternatively, processed to a dry state as by vacuum drying and terminally sterilized in the package, e.g., by gamma irradiation or electron beam (E-beam) sterilization.

In one process, the tissue is dehydrated by placing in 95 percent and then 70 percent ethanol prior to wrapping on the spherical form. The wrapped spheres are further soaked in 70 percent ethanol prior to crosslinking. In an alternate process, the tissue is presoaked in low concentration of glutaraldehyde solution before wrapping and without exposure to ethanol or other dehydrating chemicals.

The preferred material for the wraps of the invention is bovine pericardial tissue and this may be either frozen or freshly harvested. The shaping sphere is of a material that is compatible with the bovine pericardial sac tissue and resistant to the other materials used in the process. Thermoplastic acetal resins, particularly those sold under the trademark Delrin, have been successfully employed.

BRIEF DESCRIPTION OF THE DRAWINGS

In the drawings wherein like reference numerals are utilized to designate like parts throughout the same:

FIG. 3 depicts an alternate procedure for storage of the orbital implant wraps in a dry state;

FIGS. 6a and 6b are photomicrographs of a wrapped bovine pericardial tissue implant made using the regular process of FIG. 2 at 2.5× and 25×, respectively;

FIGS. 7a and 7b are photomicrographs that depict a rabbit sclera wrapped implant at 2.5× and 25×, respectively; and FIGS. 8a and 8b similarly depict a non-wrapped implant at 3.3× and normal fibrovascular and adjacent inflammatory coagulum at 25×.

DETAILED DESCRIPTION

Figure 1:
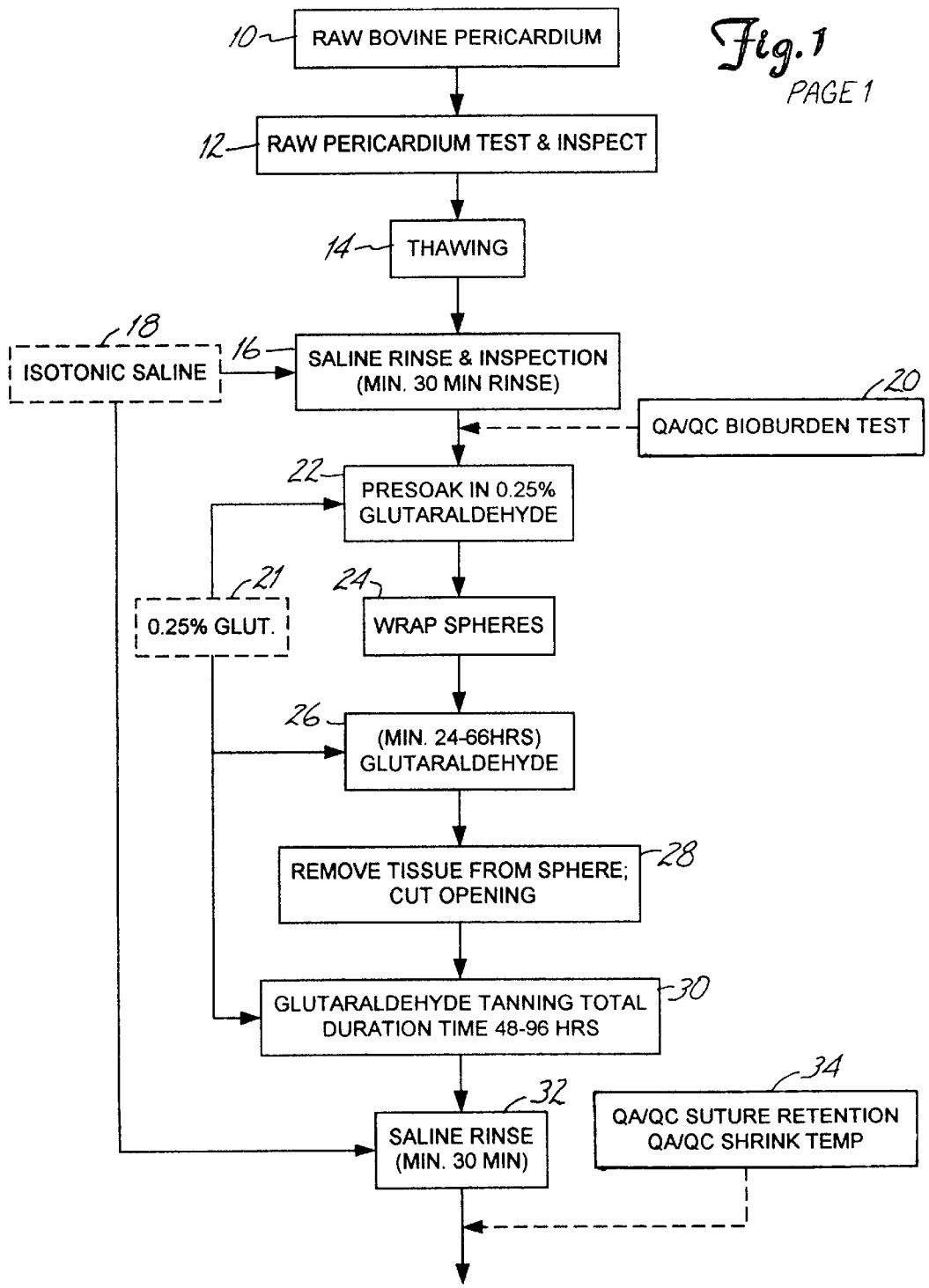
FIG. 1 depicts a process flow chart for a process for the manufacture of one type of implant wrap according to the invention.
Figure 2:
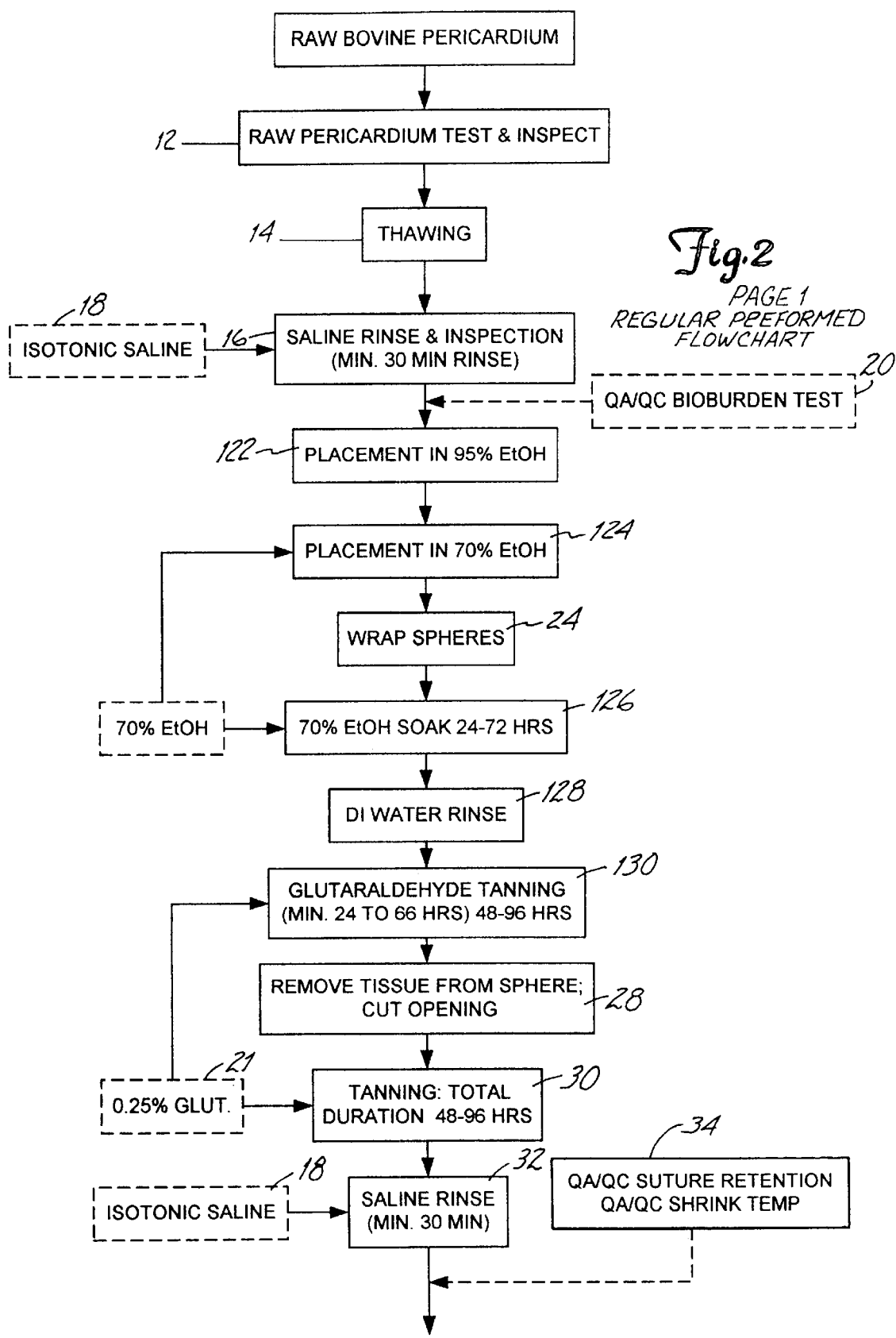
FIG. 2 is a process flow chart for producing an alternate embodiment of the implant wrap of FIG. 1.

It will be appreciated that the process for manufacturing preformed implants, including orbital implant wraps, in the preformed, crosslinked state in accordance with the process of the present invention results in a superior and more successful implant, e.g., artificial eye implant. It also greatly amplifies the implant procedure. Flow charts or diagrams describing two processes for manufacturing preformed orbital implant wrap devices in accordance with the invention are shown in FIGS. 1 and 2.

In accordance with the invention, it has been found that certain natural animal tissues, properly preserved and processed, present superior properties when it comes to orbital implant wraps particularly if manufactured in a preformed shape. In particular, bovine pericardial tissue has been used quite successfully. It will be recognized, however, that while the processes and products are described herein with particularity to the use of bovine pericardial tissue that is intended by way of example and not limitation inasmuch as it is believed that other suitable materials can be similarly processed successfully. While two distinct processes are described, they share a variety of similar or common steps, the details of which once described need not be repeated. Thus the initial collection and preservation of the tissue and sterilization and packaging of preformed wraps are generally shared by both detailed processes.

In one particularly preferred embodiment, the implant is formed from bovine pericardium, in a method as described herein, to provide the tissue with an optimal combination of biocompatability, thickness, and other physical and physiological properties.

Tissues useful as implants of this invention provide an optimal combination of chemical, physical and physiological (e.g., immunological) properties for use as implants. In a preferred sense, the tissues provide an optimal combination of such properties as suture retention, shrink temperature, circumferential tensile strength, and tensile strength, as each are determined and described herein. For instance, with regard to suture retention, particularly preferred tissues provide between about 10 g to about 200 g, and more preferably between about 30 g and about 150 g, suture retention. With regard to shrink temperature, preferred tissues provide shrink temperatures between about 70 C. and 90 C., and preferably between about 80 and about 90 C. With regard to circumferential tensile strength, preferred tissues provide between about 0.2 N/mm to about 0.5 N/mm, and more preferably between about 0.3 N/mm and about 0.4 (N/mm). Finally, preferred tissues provide tensile strengths of between about 5 MPa and about 15 MPa, and more preferably between about 7 MPa and about 12 MPa.

Implants of the present invention can be fabricated in any suitable shape or configuration, and in any suitable dimensions for their intended use. For instance, the tissue can be provided and packaged in flat (e.g., sheet or tape-like) or pre-formed form, including tubular form, with either or both major surfaces thereof being optionally textured or modified (e.g., by the covalent attachment, entrapment, and/or adsorption of biologically active factors, lubricious agents, antimicrobial agents, and the like). See, for instance, M. Valente, et al., "Detoxified Glutaraldehyde Crosslinked Pericardium: Tissue Preservation and Mineralization Mitigation in a Subcutaneous Rat Model", (*J. Heart Valve Dis.* May 1998; 7, (3):283–91), and C. Stacchino et al., "Detoxification Process for Glutaraldehyde-treated Bovine Pericardium: Biological, Chemical and Mechanical Characterization", *J. Heart Valve Dis.* Mar. 1998; 7, (2):190–4, the disclosures of each of which are incorporated herein by reference. These articles describe the manner in which glutaraldehyde promotes calcification by the action of toxic aldehyde group residuals from crosslinking. The authors have found that post-fixation treatment with homocysteic acid (HA), besides bonding aldehyde groups and neutralizing toxicity, can enhance biocompatibility due to the strongly electronegative sulfonic group. Moreover, the tissue can be provided with markings or other suitable means to indicate its preferred orientation or direction.

Tissues are preferably fixed, e.g., by crosslinking, in order to improve their biocompatability. Suitable crosslinking agents include, for instance, aldehydes such as glutaraldehyde, epoxides, isocyanates, carbodiimides, isothiocyanates, glycidalethers, and acyl azides. Tissues can be fixed at any suitable point, e.g., prior to or after being cleaned, formed, or positioned upon a form or mandrel. In a preferred embodiment, for instance using pericardium, the tissue is crosslinked after it has been positioned and crimped onto the form, or a suitable mandrel.

When used in pre-formed, e.g., tubular form, for instance, the implant can be either seamless or seamed, and is typically adapted to be positioned over a prosthetic device, e.g., stent or orbital implant, of a particular size or size range. Tissues can be formed into tubes, for instance, by sealing a flat tissue in a cylindrical form, e.g., by the use of sutures, or in a sutureless fashion as by the use of an adhesive.

In a further preferred embodiment Applicants include yet another step in the processing of pericardium. This step includes treating the tissue with a disinfecting agent, e.g., sodium hydroxide, in order to further lessen the already minimal possibility of bovine spongiform encephalitis (BSE) infection. Such treatment is not only effective as an treatment effective to reduce/eliminate BSE infectivity when used in this manner, but moreover, that a tissue thus treated provides improved or comparable properties as compared to untreated tissues. Particularly preferred tissues include fibro-serous and serous membranes, including fibro-serous membranes such as pericardium (e.g., bovine pericardium) and serous membranes such as peritoneum (e.g., porcine peritoneum). Such tissues are preferably obtained, prepared, and/or treated in a manner that renders the tissues biocompatible, e.g., substantially nonantigenic. By the term "substantially nonantigenic" it is meant that the tissue does not elicit an antigenic or other physiological response on the part of the host, to an extent that would render the cover unsuitable for its intended use. An implant of this invention can either be permanent or temporary (e.g., removable or biodegradable over a period of weeks, months or years). Optionally, in turn, such tissues can also be decellularized and/or crosslinked.

In accordance with the manufacture of the occular implant wraps of the invention, it is important to obtain consistent high quality starting material. The starting material is obtained from slaughtered animals and it is necessary to preserve the condition of the harvested animal tissue. As shown at 10 in FIGS. 1 and 2, the preferred starting material is raw bovine pericardial tissue. This tissue must meet certain minimum standards and is generally harvested from United States Department of Agriculture (USDA) inspected cattle that are at least one year old, which have been processed by selected slaughterhouses. The harvesting should occur within two hours of slaughter and the harvested tissue must be of a minimum size in order to be useful for processing into the wraps of the invention. The harvested sacs are placed in ice water immediately after collection and the water/saline solution is frequently changed to remove residual blood. The tissue is thereafter packaged in containers which maintain a temperature in the range of 32°–55° F. (2–5° C.) and shipped to arrive for processing, preferably within 72 hours after collection.

Incoming raw pericardium at 10 is initially tested and inspected as indicated at step 12 in FIGS. 1 and 2 and in accordance with a raw pericardium testing and inspection procedure that includes inspection of the material in a controlled environment for size, discoloration, environmental debris or parasites, cuts or tears (that would not afford a minimum area for use) and thickened, rough fatty or fibrous tissue. Certificates of origin and other documents are verified. The tissue is then ready for further processing.

It should be noted that pericardial tissue may also be received in a frozen state. Frozen tissue may be stored for up to, but generally no longer than, six months by which time it must be thawed and processed or discarded. The thawing step (step 14) applies only to frozen tissue. Tissue received fresh generally must be processed within about 72 hours from the completion of harvest at the slaughterhouse.

In processing frozen tissue, freezer bags containing the frozen pericardial sacs are placed directly in the refrigerator and permitted to thaw for up to about 72 hours. Thereafter, if pericardial tissue is still frozen, thawing may be continued in temperate water, as indicated. Alternatively, and expeditiously, the freezer bags can be placed directly into a container of temperate saline for 1–2 hours, the pieces being separated upon thawing. Thawed tissue is thereafter inspected in the same manner as fresh raw tissue (step 12), except that the pieces must also be checked for evidence of any freezer burn that might have occurred, as this renders them unusable.

Thawed, and/or fresh inspected pericardial tissue is then subjected to a plurality of saline rinses at stop 16 utilizing isotonic saline supplied at is. The rinses are performed in order to leach away any residual blood, and the minimum soaking time for each rinse should be approximately 30 minutes. In the case of frozen tissue, the series of cold isotonic saline rinses normally includes 2–5 rinses. If fresh tissue is used, usually 1–3 isotonic saline rinses suffice. More rinses may be used, in either case, if necessary, to remove all of the blood.

If the material is to be further processed according to the supple process of FIG. 1 (in contrast to the regular processing of FIG. 2), the material may be allowed to remain in the last saline rinse until all the pieces for a batch have been processed.

At this point in the process, a quality assurance or quality control bioburden test is performed on samples of the material, as at 20, to assure that the maximum bioburden is not exceeded by the material. Typically, the bioburden needs to be less than $1.0 \times 10^8$ CFU/gram of sac tissue. This is based on a randomly selected sample of approximately 10 grams representing material from each control number batch. These tests are conducted in a well-known manner.

The supple process of FIG. 1 will be detailed next. This will be followed by a discussion of the portions or elements of the regular process which differ and the alternative or dry storage processing.

At this juncture, the processing of the supple wraps as depicted in FIG. 1 differs somewhat from the regular processing of FIG. 2. In FIG. 1, the isotonic saline-rinsed bovine pericardial tissue is transferred from the container in the final saline rinse of step 16 to trays containing approximately 0.25% glutaraldehyde solution for a minimum of 15 minutes but no longer than about 45 minutes prior to wrapping. This occurs at step 22 of FIG. 1.

In step 24, after 15 and before 45 minutes in the approximate 0.25% glutaraldehyde solution, the tissue, which has a shiny, visceral or inside surface and a dull, parietal or outside surface, are sequentially removed and placed on a cutting board where they are again inspected for holes, thick or thin areas, or peeling or freezer burned areas. Any extraneous tissue is cleared away from both sides of the pericardial tissue at this time.

Figure 5:
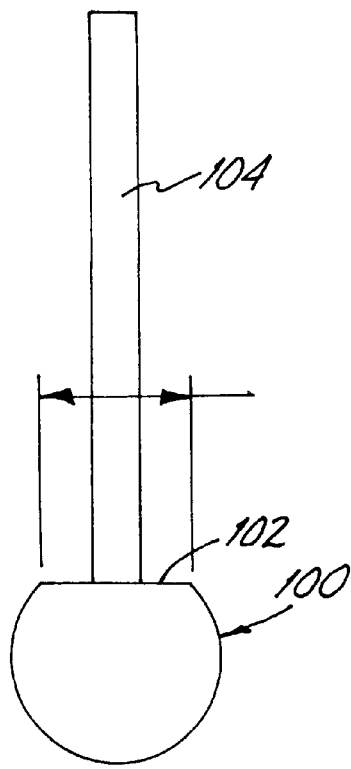
FIG. 5 depicts a spherically shaped device for use in forming the orbital implant wraps of the invention.

Pre-forming of the orbital implant wraps is now undertaken. In this part of the process, bovine pericardial tissue is wrapped around a spherically shaped device for shaping prior to further processing. One spherical shape form is illustrated at 100 in FIG. 5 and is generally made of a polymer material that is inert to the bovine pericardial tissue and also to the chemical materials utilized in the process. The material must also be mechanically stable during processing. Although other materials can be used, thermoplastic acetal resins, particularly those sold under the trademark Delrin, have been found especially useful. These spherical shaped devices or forms 100 can be provided in various sizes and are usually provided with a flat side 102. A stainless steel rod 104 is screwed into the flat side 102 of the sphere 100 for handling. Successful devices have been made using type 316 stainless steel.

In step 24, the pericardial tissue is wrapped visceral side out around the spherical form by draping it over the sphere and allowing excess tissue to hang over the sphere. once the sphere is wrapped, a conventional nylon cable tie or any suitable external retention device can be utilized to gather and secure the ends of section of pericardial tissue in place about the rod at the flat section 102. During this step wrinkles and gathers of tissue are evened out but the tissue itself is not stretched. This occurs as the retention device is being tightened. Thereafter, excess tissue may be trimmed, leaving approximately 1–3 cm of tissue hanging from or extending beyond the tie area. The tissue-wrapped sphere is placed in a fixation tank containing approximately 0.25% glutaraldehyde solution, typically by placing the rod end into one of a pattern of holes in a fixation holder board provided at the bottom of the fixation tank.

At this point an additional (approximately 0.25%) glutaraldehyde solution is added to insure that all covered spheres are fully immersed. The wrapped spheres are allowed to remain in the glutaraldehyde solution at room temperature for a minimum of 24 hours and up to a maximum of about 66 hours (step 26) prior to removal of the tissue from the sphere.

Next, as shown by step 28, the spheres are removed from the glutaraldehyde solution and the tissue is then removed from the sphere forms. This is accomplished by removing the retention device and cutting away the excess tissue near the tie area. A circular cutting device is fitted over the rod and guided down toward the tissue on the sphere. All of the tissue not covering the sphere should fit into the cutter. If not, the excess must be trimmed off. The cutter is then used to produce a circular opening of the desired size (see "B" in FIGS. 4a–4c) in the pouch covering the sphere. The tissue cutter is then removed and any necessary trimming may be accomplished using a scissors to provide a uniform round opening. This will allow the tissue sphere to be removed from the spherical shaped device and the removed spheres are then returned to containers containing glutaraldehyde solution, at step 30 for a duration time from about 30 to about 72 hours in the approximately 0.25% glutaraldehyde solution. Total glutaraldehyde exposure, both on or off the spherical form should not exceed 96 hours.

The tissue spheres now fully crosslinked are emptied of glutaraldehyde solution and thereafter subjected to a rinse at step 32 in which they are soaked for a minimum of 30 minutes in a saline solution which may be the same strength isotonic saline utilized in step 16 as the initial rinse.

At this juncture as shown at step 34, a number of spheres are removed and tested for suture retention and shrinkage. These spheres are subjected to testing after they are placed in a test tube/sample container of 70 percent ethanol (EtOH) plus 1 percent propylene oxide (PO) solution.

After a minimum of 30 minutes in the saline solution, the saline is drained off and excess saline removed by agitating or gently squeezing the spheres. At this point and as shown by step 36 in FIG. 1, the spheres are treated with a solution from 37 of 70 percent EtOH and 1 percent PO for a period from about 48 to about 432 hours (2 to 18 days). Air bubbles are removed to make sure that each sphere sinks to the bottom and is covered with the solution. After the initial 48 hour period in 70 percent EtOH plus 1 percent PO, spheres may be inspected (step 38) and the processed spheres are placed and stored thereafter in jars (step 40) filled with solution (70% EtOH+1% PO) for a minimum of 75 hours. During the solution treating phases in jars, autoclaved polymer (Delrin) mandrels may be placed inside the sphere openings to allow the solutions to fill the spheres and to eliminate air bubbles.

Thereafter the spherical wraps are subjected to another quality assurance and quality control pre-sterilization inspection at 44 during the minimum 75 hour storage time. The jarred inspected spheres are then emptied of solution and refilled with 70% ethanol/plus 1% PO for a minimum of 14 days as shown in step 46. After this has been accomplished a quality assurance sterility check is conducted and the inspected pre-shaped spheres are then subjected to a sterile water rinse for a minimum of 2 hours at 50 utilizing a water plus 1% PO solution supplied at 52. Thereafter a final water solution is provided for storage of the completed supple spheres at 54. The caps are torqued in accordance with established procedures at 56. An inspection by quality assurance and quality control is conducted at 58. Finally, the package is labeled and the final inspection and release to stores is conducted at 62.

After step 20, the process for the regular pre-formed orbital implant wraps differs from that for the supple orbital implant wraps. The remaining portion of the flow chart for the regular process will now be described (FIG. 2). Instead of pre-soaking the inspected material in approximately 0.25% glutaraldehyde solution, the material forming the regular spheres is, instead, subjected to an initial dehydration step by placement in a solution of 95 percent ethanol as shown in FIG. 2 at 122.

In this step the pericardium is transferred from the final saline rinse to the 95 percent ethanol solution after being gently squeezed to remove any excess saline. The mixture is agitated for 1 minute and the pericardial tissue is allowed to soak in the 95 percent ethanol solution for approximately 15 minutes after which it is removed and placed in the 70 percent ethanol solution 125 in accordance with step 124 where it is further agitated for an additional 1 minute. The pericardial tissue is removed from the 70 percent ethanol solution and subjected to a wrapping step 24 which corresponds to the wrapping step previously described in conjunction with the manufacture of the supple pre-formed orbital implant wrap, above. This produces wrapped, tied and trimmed spheres which are thereafter ready for additional processing. These wrapped spheres are returned to a solution of 70 percent ethanol at 126 where they are soaked for a period of from 24 to about 72 hours prior to further processing. Thereafter, at 128 the ethanol-soaked tissue wrapped spheres are subjected to a deionized water rinse. This may be accomplished by draining the ethanol from the tank and allowing deionized water to rinse the wrapped spheres until the tank fills and then allow the water to drain. The tank may then be re-filled as at 130 with glutaraldehyde crosslinking solution where it is allowed to remain at room temperature for a minimum of 24 hours and a max of 66 hours prior to the removal of the tissue from the spheres, in accordance with step 26 previously described. Thereafter, the tissue is removed from the sphere and the opening cut as previously described in conjunction with step 28 for the supple sphere process. Steps comparable to previously described steps 30 and 32 are also followed as is the quality assurance step 34.

The remainder of the steps contained in the procedure for the regular pre-formed orbital implant wraps in accordance with the present invention are basically the same as those described in conjunction with FIG. 1 numerated in steps 36–62.

FIG. 3 depicts an alternative procedure for processing the preformed, crosslinked occular implant wraps for storage in a dry state. After the 14-day 70% EtOH+1% PO treatment of step 46, either the regular or supple material may be rinsed twice in sterile, filtered and deionized water at 148. The duration for the first rinse is at least 2 hours and for the second rinse is at least one hour. Total rinse time may not exceed 48 hours. The tissue wraps are then dried at step 150 by any suitable means as by vacuum drying. Success has been achieved by subjecting the processed warps to a vacuum of 115 millitorr for about two hours. The moisture contents is monitored as indicated at 152 after the drying step. The dried wraps are then packaged in air-tight and moisture resistant packaging at step 154 in which the oxygen content, moisture content and bioburden are sample-verified at step 156. The packaged occular implant wraps are then sterilized by electron beam or other suitable method in step 158 and, thereafter, samples are checked for suture retention, shrink temperature, moisture content and pyrogenicity at 160. Final inspection of the product is conducted in step 162.

EXAMPLES

Example 1
Rabbit Study, Peri-Guard as an Orbital Implant Wrap

A rabbit study was performed to compare wraps of the invention and homologous sclera for use as an orbital implant wrap.

Eighteen New Zealand white rabbits were unilaterally enucleated. Each of the rabbits received a 12 mm hydroxyapatite sphere (wrapped or unwrapped). Six rabbits received an implant wrapped in homologous rabbit sclera; six rabbits received implants wrapped in bovine pericardium (regular process); and six rabbits received non-wrapped implants. The hydroxyapatite sphere was implanted into the muscle cone of the orbit. Tenon's capsule and conjunctiva were closed in separate layers over the implant.

The rabbits were sacrificed seven weeks later and observations were made of the clinical appearance of the socket. The socket was then exenterated and the specimens immersed in isopropyl alcohol. Histopathologic analysis was carried out by a pathologist blinded to the treatment groups.

The clinical appearance of the sockets were similar among the three treatment groups. All three groups tolerated the implants well, with minimal inflammation. However, one of the non-wrapped implants became exposed. No implants extruded.

The implants wrapped with bovine pericardium (regular process) and homologous rabbit sclera displayed a well delineated fibrous capsule on histopathologic analysis. Each non-wrapped implant showed focal regions which lacked capsule formation. Wrapped implants displayed more disruption of the lamellae of the wrapping material and slightly more inflammation in the outer portion of the wrapping material than did the sclera-wrapped implants (refer to FIGS. 6a and 6b and 7a and 7b). The lamellar disruption within the regular process bovine wrapped material and the inflammation in the orbital tissues immediately adjacent to the region did not appear to affect the clinical outcome or the fibrovascular ingrowth into the implant.

Fibrovasculair ingrowth to the center of the implant was seen in all wrapped implants. In one of the non-wrapped implants, a tract of nonvascularized hydroxyapatite extended to the center of the implant. An inflammatory coagulum was present in the interstices of the implant along this tract (refer to FIGS. 8a and 8b).

The results of this study show that bovine pericardium appears to function similarity to donor sclera as a wrapping material for hydroxyapatite spheres in anophthalmia sockets. While lamellar disruption within the wrapping material, and inflammation in the orbital tissues immediately adjacent to the region was more evident with bovine pericardium, this did not appear to affect the clinical outcome or the fibrovascular ingrowth into the implant.

While the rabbit study was performed using regular processed wrap material, the supple wrap material product has been found to be substantially equivalent to the regular wrap material.

Figure 4A:
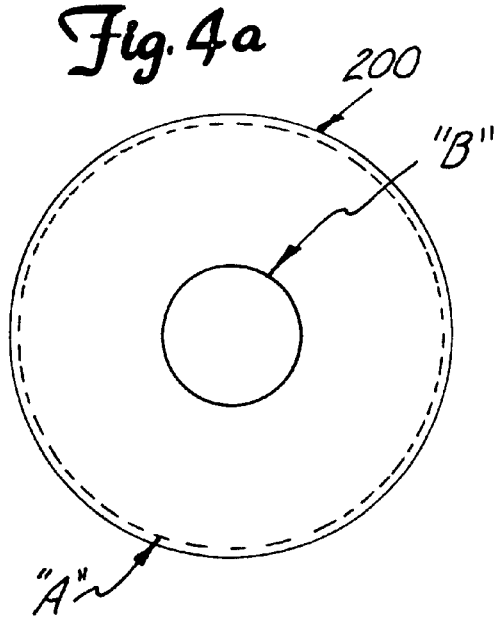
FIGS. 4a–4c depict an orbital implant wrap made in accordance with the invention.
Figure 4B:
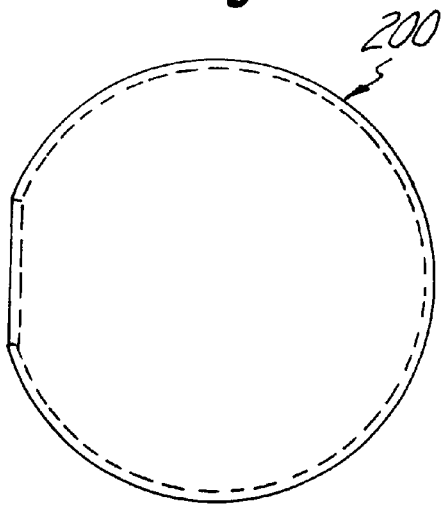
Figure 4C:
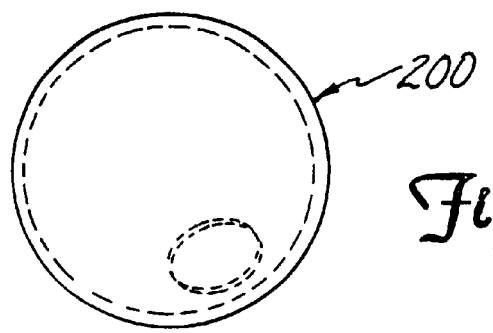

FIGS. 4a–4c depict several views of an orbital implant wrap 200 manufactured by either of the pre-forming sphere processes of the present invention. In accordance with the invention, the inside diameter "A" of the sphere along with the diameter of the opening "B" can be varied as required to accommodate a variety of sizes of replacement eye devices. Typical size ranges are from about 14 mm to 22 mm inside diameter A and 8–10 mm with regard to the hole diameter B. The typical thickness is from about 0.2 to about 0.8 mm for the processed pericardial tissue.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. An implant material comprising a natural animal tissue crosslinked in position upon a form or mandrel into a pre-formed shape of the form or mandrel, the tissue substantially retaining said shape when implanted into a body.

2. An implant material according to claim 1 wherein the natural animal tissue is selected from the group consisting of fibro-serous and serous membranes.

3. An implant material according to claim 2 wherein the tissue comprises a fibro-serous membrane comprising pericardium.

4. An implant material according to claim 1 wherein the tissue is crosslinked using a crosslinking agent selected from the group consisting of aldehydes, epoxides, isocyanates, carbodiimides, isothiocyanates, glycidalethers, and acyl azides.

5. An implant material according to claim 1 wherein the material is provided in sterile form and is adapted to be implanted into a body and attached in place.

6. An implant material according to claim 1 wherein the implant is provided in the form of a wrap or implantable sac.

7. An implant material according to claim 6 wherein the material is provided in a spherical form and is adapted to wrap an orbital implant.

8. An implant material according to claim 1 wherein the natural animal tissue is selected from the group consisting of fibro-serous and serous membranes and the tissue is crosslinked using a crosslinking agent selected from the group consisting of aldehydes, epoxides, isocyanates, carbodiimides, isothiocyanates, glycidalethers, and acyl azides.

9. An implant material according to claim 8 wherein the material is provided in sterile form and is adapted to be implanted into a body and attached in place.

10. An implant material according to claim 9 wherein the material is provided in a spherical form and is adapted to wrap an orbital implant.

11. An implant material according to claim 1 wherein the natural animal tissue is selected from the group consisting of fibro-serous and serous membranes, the tissue is crosslinked using a crosslinking agent selected from the group consisting of aldehydes, epoxides, isocyanates, carbodiimides, isothiocyanates, glycidalethers, and acyl azides, and the material is provided in sterile form and is adapted to be implanted into a body and attached in place.

12. An implant material according to claim 11 wherein the implant is provided in the form of a wrap or implantable sac.

13. A process for preparing an implant material, comprising the steps of forming a natural tissue into a preformed shape upon a form or mandrel and crosslinking the formed tissue in order to retain the shape of the form or mandrel, the tissue substantially retaining said shape when removed from the form or mandrel and/or when implanted into a body.

14. A process according to claim 13 wherein the process comprises the steps of wrapping the natural tissue on a shaping form, crosslinking the wrapped tissue in place upon the form, removing the tissue from the shaping form, and further crosslinking the removed tissue.

15. A process according to claim 14 comprising the further steps of dehydrating the tissue in ethanol prior to wrapping on the shaping form, and soaking the tissue in ethanol prior to further crosslinking.

16. A process according to claim 14 comprising the further steps of presoaking the tissue in a solution of crosslinking agent prior to wrapping, without dehydrating or exposure to ethanol.

17. A process according to claim 14 comprising the further steps of rinsing, sterilizing and packaging the implant in a water solution.

18. A process according to claim 13 comprising the further steps of processing the crosslinked tissue to a dry state, packaging the dry tissue, and resterilizing the packaged, dry tissue by electron beam sterilization.

19. A process according to claim 13 comprising the further step of treating the tissue with a disinfecting agent.

20. A combination comprising an orbital implant wrapped with a pre-formed tissue prepared according to the process of claim 13.

21. A process according to claim 13 wherein the natural animal tissue is selected from the group consisting of fibro-serous and serous membranes, the tissue is crosslinked using a crosslinking agent selected from the group consisting of aldehydes, epoxides, isocyanates, carbodiimides, isothiocyanates, glycidalethers, and acyl azides, and the material is provided in sterile form and is adapted to be implanted into a body and attached in place.

22. A process according to claim 21 wherein the implant is provided in the form of a wrap or implantable sac.

23. A process according to claim 21 wherein the process comprises the steps of wrapping the natural tissue on a shaping form, crosslinking the wrapped tissue in place upon the form, removing the tissue from the shaping form, and further crosslinking the removed tissue.

24. A process according to claim 23 wherein the process comprises the further steps of a) dehydrating the tissue in ethanol prior to wrapping on the shaping form, and soaking the tissue in ethanol prior to further crosslinking and b) presoaking the tissue in a solution of crosslinking agent prior to wrapping, without dehydrating or exposure to ethanol.

25. A process according to claim 23 comprising the further steps of rinsing, sterilizing and packaging the implant in a water solution.

26. A process according to claim 23 comprising the further steps of processing the crosslinked tissue to a dry state, packaging the dry tissue, and resterilizing the packaged, dry tissue by electron beam sterilization.

27. A process according to claim 23 comprising the further step of treating the tissue with a disinfecting agent.

* * * * *